(12) United States Patent
Chen

(10) Patent No.: US 7,550,641 B2
(45) Date of Patent: Jun. 23, 2009

(54) METHODS FOR RECOVERING ACTIVITY OF MOLECULAR SIEVE CATALYSTS

(75) Inventor: John Q. Chen, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/123,545

(22) Filed: May 20, 2008

(65) Prior Publication Data

US 2008/0227934 A1    Sep. 18, 2008

Related U.S. Application Data

(62) Division of application No. 11/171,886, filed on Jun. 30, 2005.

(51) Int. Cl.
*B01J 38/06* (2006.01)
*B01J 38/48* (2006.01)
*B01J 38/66* (2006.01)
*C07C 1/00* (2006.01)

(52) U.S. Cl. .......................... 585/640; 502/20; 502/22; 502/26; 502/34; 502/27; 502/54; 502/55

(58) Field of Classification Search ................ 502/20, 502/22, 26, 27, 34, 55, 54; 585/640
See application file for complete search history.

(56) References Cited

U.S. PATENT DOCUMENTS

| | | | |
|---|---|---|---|
| 3,493,490 A | 2/1970 | Plank et al. ................ 208/120 |
| 4,055,482 A | 10/1977 | Robson ...................... 208/111 |
| 4,310,440 A | 1/1982 | Wilson et al. ............... 252/435 |
| 4,440,871 A | 4/1984 | Lok et al. ................... 502/214 |
| 4,477,582 A | 10/1984 | Miale ......................... 502/26 |
| 4,567,029 A | 1/1986 | Wilson et al. ............... 423/306 |
| 4,681,864 A | 7/1987 | Edwards et al. ............... 502/63 |
| 4,861,743 A | 8/1989 | Flank et al. ................. 502/214 |
| 4,871,702 A | 10/1989 | Chang et al. .................. 502/86 |
| 5,096,684 A | 3/1992 | Guth et al. .................. 423/306 |
| 5,126,308 A | 6/1992 | Barger et al. ................ 502/214 |
| 5,185,310 A | 2/1993 | Degnan et al. .............. 502/214 |
| 6,498,120 B1 | 12/2002 | Janssen et al. ................ 502/22 |
| 6,639,117 B2 | 10/2003 | Janssen et al. .............. 585/639 |
| 6,756,516 B2 | 6/2004 | Mees et al. ................. 585/640 |
| 6,825,391 B2 | 11/2004 | Janssen et al. .............. 585/640 |

*Primary Examiner*—In Suk Bullock
(74) *Attorney, Agent, or Firm*—Mark Goldberg

(57) ABSTRACT

The invention is directed to a method of rejuvenating silicoaluminophosphate molecular sieve catalyst that has been deactivated hydrothermally as well as a method of using the rejuvenated catalyst to make an olefin product from an oxygenate feed. In particular, the invention is directed to rejuvenating the catalyst by contacting it with warm water, ammonium salts, dilute acids or low pressure steam until the catalytic activity level of the catalyst has been increased to the desired extent.

16 Claims, No Drawings

METHODS FOR RECOVERING ACTIVITY OF MOLECULAR SIEVE CATALYSTS

CROSS-REFERENCE TO RELATED APPLICATION

This application is a Division of copending application Ser. No. 11/171,886 filed Jun. 30, 2005, the contents of which are hereby incorporated by reference in its entirety.

FIELD OF THE INVENTION

The invention is directed to a method of rejuvenating silicoaluminophosphate molecular sieve catalyst that has been deactivated hydrothermally as well as a method of using the rejuvenated catalyst to make an olefin product from an oxygenate feed. In particular, the invention is directed to rejuvenating the catalyst by contacting it with warm water, ammonium salts, or low pressure steam until the catalytic activity level of the catalyst has been increased to the desired extent.

BACKGROUND OF THE INVENTION

Silicoaluminophosphates (SAPOs) have been used as adsorbents and catalysts. As catalysts, SAPOs have been used in processes such as fluid catalytic cracking, hydrocracking, isomerization, oligomerization, the conversion of alcohols or ethers, and the alkylation of aromatics. The use of SAPOs in conversion of oxygenates to light olefin products, particularly ethylene and propylene, is becoming of greater interest for large scale, commercial production facilities. Catalysts deactivate during use due to various reasons. Some catalysts are sensitive to exposure to moisture while other catalysts are impacted by the operating conditions in a reactor. In the methanol to olefins (MTO) process, for example, SAPO-34 catalyst deactivation can be divided into two types: 1) short term deactivation due to coking; 2) long term deactivation due to hydrothermal aging. The short term deactivation can be completely reversed by careful coke burning. Activity lost during hydrothermal aging is much more difficult to recover. The present invention provides a method for rejuvenating SAPO catalysts.

As is known in the development of new large scale, commercial production facilities in the commodity chemical business, many problems arise in the scale up from laboratory and pilot plant operations. Although some work has been published relating to the intermediate activities in the catalyst production-to-use chain, few of the problems associated therewith have been addressed. For example, U.S. Pat. No. 4,681,864 to Edwards et al. discuss the use of SAPO-37 molecular sieve as a commercial cracking catalyst. It is disclosed that activated SAPO-37 molecular sieve has poor stability, and that stability can be improved by using a particular activation process. In this process, organic template is removed from the core structure of the sieve just prior to contacting with feed to be cracked. The process calls for subjecting the sieve to a temperature of 400° to 800° C. within the catalytic cracking unit.

U.S. Pat. No. 5,185,310 to Degnan et al. discloses another method of activating silicoaluminophosphate molecular sieve compositions. The method calls for contacting a crystalline silicoaluminophosphate with gel alumina and water, and thereafter heating the mixture to at least 425° C. The heating process is first carried out in the presence of an oxygen depleted gas, and then in the presence of an oxidizing gas. The object of the heating process is to enhance the acid activity of the catalyst. The acid activity is enhanced as a result of the intimate contact between the alumina and the sieve.

Briend et al., J. Phys. Chem. 1995, 99, 8270-8276, teaches that SAPO-34 loses its crystallinity when the template has been removed from the sieve and the de-templated, activated sieve has been exposed to air. Data are presented which suggest that over at least the short term, this crystallinity loss is reversible. Even over a period of perhaps two years, the data suggests that crystallinity loss is reversible when certain templates are used.

Several patents assigned to ExxonMobil Chemical Company have addressed a discovery that activated SAPO molecular sieve will exhibit a loss of catalytic activity when exposed to a moisture-containing environment—both from the ambient humidity as well as the high temperature steaming environment exposed to the catalyst in the conversion of oxygenates to olefins. These patents have addressed several different methods for recovery of catalyst activity. In U.S. Pat. No. 6,639,117, the freeze drying of the catalyst is employed to recover the catalyst activity. In U.S. Pat. No. 6,498,120 and U.S. Pat. No. 6,825,391, a silicoaluminophosphate molecular sieve is rejuvenated through contact of the catalyst with an anhydrous liquid or vapor, in particular methanol. Another method is disclosed in U.S. Pat. No. 6,756,516 in which the catalyst is treated with certain organic nitrogen compounds to protect the catalyst from degradation through exposure to moisture.

Although it may be possible to use the above techniques to protect a catalyst from the exposure to moisture within an ambient atmosphere, there still remains the need to rejuvenate catalyst that has been deactivated from exposure to high temperature steam environments. Surprisingly, in light of the observations by ExxonMobil and the other prior art regarding the deactivation of SAPO catalysts by exposure to moisture, it has now been discovered that water or ammonium salts can be used to rejuvenate deactivated catalyst, especially SAPO-34 that has been deactivated by high temperature steam.

SUMMARY OF THE INVENTION

In order to overcome the various problems associated with decrease of activity of a molecular sieve due to contact with high temperature steam, this invention provides a way to rejuvenate the molecular sieve. In general, this invention provides a process for rejuvenating a molecular sieve which comprises providing a deactivated molecular sieve and contacting the molecular sieve with warm water, water vapor or ammonium salts until the catalyst activity has been increased by a desired amount.

Preferably, the molecular sieve is a silicoaluminophosphate molecular sieve and its activity is increased by at least about 25% through contact with water and preferably by more. While there may be other liquids mixed with the water, the liquid is at least 50% water. There also may be solids, such as ammonium salts dissolved in the liquid. Among the salts that may be used are ammonium nitrate, ammonium chloride ammonium phosphate, ammonium sulfate, ammonium acetate, ammonium carbonate, as well as other ammonium salts.

The silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferably, the silicoaluminophosphate is selected from the group consisting of SAPO-18, SAPO-34, SAPO-35, SAPO-44, SAPO-47, the metal containing forms thereof, and mixtures thereof. More preferably, the silicoaluminophosphate is selected from the group consisting of SAPO-18 and SAPO-34, the metal containing forms thereof, and mixtures thereof.

In addition to the rejuvenation of the catalyst, the invention comprises the use of the catalyst in making an olefin product from an oxygenate-containing feedstock. The method comprises forming a rejuvenated molecular sieve; and then contacting the rejuvenated molecular sieve with an oxygenate-containing feedstock to produce an olefin product.

The oxygenate-containing feedstock is selected from the group consisting of methanol; ethanol; n-propanol; isopropanol; $C_4$ to $C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferably, the oxygenate-containing feedstock is selected from the group consisting of methanol, dimethyl ether, and mixtures thereof.

It is also desirable that, in the method of making the olefin product, the rejuvenated molecular sieve is contacted with the oxygenate-containing feedstock at a temperature of 200° to 700° C. Preferably the rejuvenated molecular sieve is contacted with the oxygenate-containing feedstock at a WHSV of at least 5 $hr^{-1}$ and preferably at least 20 $hr^{-1}$. It is also preferred that the silicoaluminophosphate molecular sieve is provided with a binder material.

The invention also provides contacting the olefin product with a polyolefin-forming catalyst under conditions effective to form a polyolefin. The preferred olefin product contains ethylene and/or propylene, which can be used to form polyethylene and/or polypropylene. The olefin and polyolefin products so formed are also considered to be encompassed by the invention.

DETAILED DESCRIPTION OF THE INVENTION

SAPO molecular sieve catalysts, in particular, are susceptible to structural changes as a result of continued exposure to even low levels of moisture. Such authorities as Paulitz et al., MICROPOROUS MATERIALS, 2, 223-228 (1994), however, have shown through X-ray diffraction (XRD), nuclear magnetic resonance (NMR), infrared (IR) and nitrogen ($N_2$) adsorption analyses that the structural change is largely reversible.

The loss of catalytic activity as a result of contact of molecular sieve with moisture at both storage temperatures and at steaming temperatures within a reactor present a problem when large quantities of relatively expensive catalyst are needed for commercial operations. In order to overcome the various problems associated with decrease of activity of a molecular sieve due to contact with high temperature steam, this invention provides a way to rejuvenate the molecular sieve. In general, this invention provides a process for rejuvenating a molecular sieve which comprises providing a deactivated molecular sieve and contacting the molecular sieve with warm water, water vapor, dilute acid, or ammonium salts such as ammonium acetate, ammonium chloride or ammonium carbonate, ammonium phosphate, ammonium sulfate, as well as other ammonium salts, until the catalyst activity has been increased by a desired amount. Preferred dilute acids include nitric acid and hydrochloric acid that are from 0.01 to 2 N, preferably 0.01 to 1 N and most preferably from 0.01 to 0.5 N.

Preferably, the molecular sieve is a silicoaluminophosphate molecular sieve and its activity is increased by at least about 25% through contact with water and preferably by more. While there may be other liquids mixed with the water, the liquid is at least 50% water. There also may be solids, such as salts dissolved in the liquid.

SAPO molecular sieve, as well as catalyst containing SAPO molecular sieve, which exhibits decreased catalytic activity as a result of hydrothermal deactivation can be rejuvenated by contacting the sieve or catalyst with water at relatively moderate temperatures from room temperature up to 300° C. More specifically, it has been found that contact with water at a temperature from about 15° up to 200° C. can more than double the activity of the catalyst in conversion of oxygenates to olefins. Preferably the water temperature is from 25° to 100° C. and most preferably is about 65° to 90° C.

In this invention, rejuvenation is considered to be demonstrated when the rejuvenation process results in a relative increase in catalyst activity of at least 25%. Preferably, the rejuvenation process will result in an increase in catalyst activity of at least about 50%, most preferably at least about 100%, the increase being calculated as the change before rejuvenation and after rejuvenation on a percent basis.

In general the liquid water or water vapor is contacted with the molecular sieve to be rejuvenated in a batch or continuous process. In either process, the water is contacted with the molecular sieve for a time which can range from several minutes to hours or up to several weeks. Contact can be stopped at the time a desired degree of rejuvenation has been obtained. Desirably contacting continues until a relative increase in the catalyst activity of at least 25% has been obtained. Desirably, the water is flowed over the molecular sieve at temperature in the range of from about 25° to 100° C., preferably from about 65° to 90° C.

The pressure at which contact between the water in liquid or vapor form and the molecular sieve can vary. Desirably, pressure is in the range of from vacuum conditions to about 690 kPa (100 psia), preferably from about 0 to 345 kPa (0 to 50 psia).

The preferred catalyst that is used in this invention is one that incorporates a silicoaluminophosphate (SAPO) molecular sieve. The molecular sieve comprises a three-dimensional microporous crystal framework structure of [$SiO_2$], [$AlO_2$] and [$PO_2$] tetrahedral units. This type of framework is effective in converting various oxygenates into olefin products.

When a silicoaluminophosphate molecular sieve is used in this invention, it has a relatively low $Si/Al_2$ ratio. In general, the lower the $Si/Al_2$ ratio, the lower the $C_1$ to $C_4$ saturates selectivity, particularly propane selectivity. An $Si/Al_2$ ratio of less than 0.65 is desirable, with an $Si/Al_2$ ratio of not greater than 0.40 being preferred, and an $Si/Al_2$ ratio of not greater than 0.32 being particularly preferred. An $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5 to 15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

The [$PO_2$] tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The [AlO$_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [SiO$_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, intergrowths of two or more of these SAPOs and mixtures thereof. Preferred are SAPO-18, SAPO-34, SAPO-35, SAPO-44, and SAPO-47, particularly SAPO-18 and SAPO-34, including the metal containing forms thereof, intergrowths of two or more of these SAPOs and mixtures thereof.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. Among the aluminophosphates that can be included are AlPO-5, AlPO-11, AlPO-16, AlPO-17, AlPO-18, AlPO-20, AlPO-31, AlPO-34, AlPO-35, AlPO-36, AlPO-40, AlPO-41, AlPO-42, AlPO-44, and ALPO-47. A more detailed description of the background and synthesis of aluminophosphates is found in U.S. Pat. No. 4,310,440, which is incorporated herein by reference in its entirety. Some preferred ALPO structures are ALPO-5, ALPO-11, ALPO-18, ALPO-31, ALPO-34, ALPO-36, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These structures (which contain template prior to calcination) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. No. 4,440,871; U.S. Pat. No. 4,861,743; U.S. Pat. No. 5,096,684; and U.S. Pat. No. 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100° to 250° C., until a crystalline product is formed. Formation of the crystalline product can take anywhere from around two hours to as much as two weeks.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group.

Representative templates include tetraethyl ammonium compounds, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. The preferred template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the ATLAS OF ZEOLITE STRUCTURAL TYPES, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20μ to 3,000μ, more preferably about 30μ to 200μ, most preferably about 50μ to 150μ.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

It is particularly desirable that the rejuvenated molecular sieve of this invention be used in the process of making olefin product from an oxygenate-containing feedstock. In one embodiment of this invention, a feed containing an oxygenate, and optionally a diluent or a hydrocarbon added separately or mixed with the oxygenate, is contacted with a catalyst containing a rejuvenated SAPO molecular sieve in a reaction zone or location. The location in which such contact takes place is herein termed the "reactor," which may be a part of a "reactor apparatus" or "reaction system." Another part of the reaction system may be a "regenerator," wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$ to $C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making the oxygenate feedstock from hydrocarbons such as oil, coal, tar sand, shale, biomass and natural gas. Methods for making an oxygenate feedstock are known in the art. These methods include fermentation to alcohol or ether, making synthesis gas, and then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 mol-%, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be introduced in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary.

Any standard reactor system can be used, including fixed bed, fluid bed or moving bed systems. Reactors that can be used include riser reactors and short contact time countercurrent free-fall reactors in which an oxygenate feedstock can be contacted with a molecular sieve catalyst at a WHSV of at least about 5 $hr^{-1}$, preferably in the range of from about 20 to 1000 $hr^{-1}$, and most preferably in the range of from about 20 to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the rejuvenated catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° to 700° C., preferably from about 300° to 600° C., more preferably from about 350° to 550° C. At the lower end of the temperature range, the formation of the desired olefin products may become markedly slow. At the upper end of the temperature range, the process may not form an optimum amount of product. The pressure also may vary over a wide range, including autogenous pressures.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with the feed. Typical regeneration temperatures are in the range of 250° to 700° C., desirably in the range of 350° to 700° C. Preferably, regeneration is carried out at a temperature range of 450° to 700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10° to 200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator. The catalyst may also be cooled with water in accordance with the present invention.

The reactor and regenerator may be configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred the catalyst within the reactor have an average level of coke effective for selectivity to ethylene and/or propylene. The average coke level on the catalyst will be from about 2 to about 10 wt-%. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt-%.

In order to make up for any catalyst loss during the regeneration or reaction process, fresh catalyst can be added. The fresh catalyst may either be added to the regenerated catalyst after it is removed from the regenerator, and then both are added to the reactor or the fresh catalyst may be added to the reactor independently of the regenerated catalyst.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following example, which is intended to illustrate specific embodiments within the overall scope of the invention as claimed.

EXAMPLE

A SAPO-34 catalyst was obtained that was made according to the following process: In a container orthophosphoric acid (85%) was combined with water. To this there was added a silica sol and a 35 wt. % aqueous solution of tetraethylammonium hydroxide (TEAOH). Finally, alumina in the form of pseudo-boehmite along with water and SAPO-34 seed material were added and blended in. The mixture was now placed in a steel pressure reactor equipped with a turbine stirrer. The mixture was now stirred and heated to 100° C. over a 6 hour period, held at 100° C. for 6 hours, then heated to 175° C. over a period of 3 hours and held there for the reaction time of 24 hours. Finally, the reaction mixture was cooled to ambient temperature and the solid product recovered by centrifugation and washed with water. Then, a coked MTO catalyst, removed from a demonstration plant, that comprised 40 wt-% SAPO-34+ binder was first calcined to remove coke (Sample I). The sample was then hydrothermally treated at 700° C., 1 atm $H_2O$ for 800 hours (Sample II). A series of treatments as outlined below were done to the hydrothermally deactivated sample. All treated samples were then dried at 120° C. overnight and followed by exposure to ambient conditions for 48 hours to achieve a consistent LOI on the samples. The samples were then sent for a microreactor test to determine activity of the sample.

Sample and treatment description and catalyst activity

| Sample # | Description | K-Oxygenate (volumetric rate constant 1/s) |
|---|---|---|
| 1 | Starting material that has been regenerated (550° C., 15 hours). Dried at 120° C., then left at room temperature for 48 hours. | 370 |
| 2 | Regenerated catalyst is steamed at 700° C. for 800 hours at 1 atm water pressure. Dried at 120° C., then at room temperature for 48 hours. | 106 |
| 3 | Rejuvenated with distilled water at room temperature for 4 hours, washed 5 times with 50 ml distilled water, dried at 120° C., then left open to air for 48 hours. | 144 |
| 4 | Rejuvenated with distilled water at 85° C. for 4 hours, washed 5 times with 50 ml distilled water, dried at 120° C., then left open to air for 48 hours. | 204 |
| 5 | Rejuvenated with hot 2N $NH_4NO_3$, dissolved in distilled water at 85 C. for 4 hours, washed 5 times with 50 ml distilled water, dried at 120° C., then left open to air for 48 hours, calcined at 650° C. for 5 hours, left open to air for 48 hours. | 195 |
| 6 | Rejuvenated with steaming at 150° C. for 4 hours in $N_2$, 25% steam (200 torr $H_2O$) dried at 120° C., then left open to air for 48 hours. | 125 |
| 7 | Rejuvenated with steaming at 200° C. for 4 hours in $N_2$, 25% steam (200 torr $H_2O$) dried at 120° C., then left open to air for 48 hours. | 126 |

In the microreactor reactivity test, 150 mg of catalyst is loaded into a 8 mm ID quartz reactor with sintered glass frit at the middle of the reactor to keep catalyst in place. Catalyst is first pretreated at 500° C. for 1 hour in dry $N_2$. Reactor temperature is then lowered to 450° C. and methanol feed is introduced. Methanol feed is introduced by passing a stream of $N_2$ (350 cc/min) through a 3-leg saturator filled with methanol and set in at 5° C. constant temperature bath. An online GC is attached to the plant for product analysis. According to literature, reaction rate is assumed to be first order with regard to oxygenates concentration. Catalyst activity is expressed as first order kinetic constant for oxygenates conversion which is expressed by the equation $-kt=\ln(1-x)$ where x is oxygenate conversion, t is space time and k is a first order kinetic constant. First order kinetic constant for all the catalysts tested are summarized in the above table. Oxygenates conversion was determined on a water and coke free basis. It is clear that treatment of the hydrothermally deactivated catalysts with water or with water containing ammonium salts resulted in recovery of significant amount of lost activity. It is anticipated that such way for catalyst activity recovery can be applied to other SAPO based molecular sieves.

This invention can be applied in commercial operation where hydrothermally deactivated catalyst coming out of regenerator can be treated with warm water and the treated catalyst can be returned back to regenerator or reactor directly.

The invention claimed is:

1. A method of making an olefin product from an oxygenate-containing feedstock, comprising:
   providing a silicoaluminophosphate molecular sieve having decreased catalytic activity as a result of contact with high temperature moisture at between 300° and 600° C. or regeneration temperatures between 350° and 700° C.;
   contacting the molecular sieve with low temperature liquid comprising at least 50% water or water vapor wherein said low temperature is between about 15° and 200° C. until the catalytic activity of said molecular sieve increases at least 25% as compared to the molecular sieve having decreased catalytic activity; and
   then contacting the rejuvenated molecular sieve with an oxygenate-containing feedstock to produce an olefin product.

2. The method of claim 1 wherein said low temperature liquid further comprises at least one dissolved solid.

3. The method of claim 1 wherein said dissolved solid is selected from the group consisting of ammonium chloride, ammonium phosphate, ammonium sulfate, ammonium acetate, ammonium carbonate, ammonium nitrate and mixtures thereof.

4. The method of claim 1 wherein said low temperature liquid is a dilute acid.

5. The method of claim 4 wherein said dilute acid is nitric acid or hydrochloric acid.

6. The method of claim 1 wherein after said molecular sieve is contacted with low temperature water, said molecular sieve is sent to a regeneration zone for removal of coke formed on said molecular sieve.

7. The method of claim 1 wherein the catalytic activity is increased by at least 50%.

8. The method of claim 1 wherein the catalytic activity is increased by at least 100%.

9. The method of claim 1 wherein the low temperature is between 25° and 100° C.

10. The method of claim 1 wherein the low temperature is between 65° and 90° C.

11. The method of claim 1 wherein the silicoaluminophosphate molecular sieve is selected from the group consisting of SAPO-5, SAPO-8, SAPO-1, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, intergrowths of two or more of said silicoaluminophosphate molecular sieves and mixtures thereof.

12. The method of claim 1 wherein the silicoaluminophosphate molecular sieve is selected from the group consisting of SAPO-18 and SAPO-34, the metal containing forms thereof, intergrowths and mixtures thereof.

13. The method of claim 1 wherein the oxygenate-containing feedstock is selected from the group consisting of methanol; ethanol; n-propanol; isopropanol; $C_4$ to $C_{20}$ alcohols; methyl ethyl ether; dimethyl ether; diethyl ether; di-isopropyl ether; formaldehyde; dimethyl carbonate; dimethyl ketone; acetic acid; and mixtures thereof.

14. The method of claim 1 wherein the rejuvenated molecular sieve is contacted with the oxygenate-containing feedstock at a temperature of 200° to 700° C.

15. The method of claim 1 wherein the silicoaluminophosphate molecular sieve is provided with a binder material.

16. The method of claim 1 wherein the olefin product is contacted with a polyolefin-forming catalyst under conditions effective to form a polyolefin.

* * * * *

UNITED STATES PATENT AND TRADEMARK OFFICE
CERTIFICATE OF CORRECTION

PATENT NO. : 7,550,641 B2  Page 1 of 1
APPLICATION NO. : 12/123545
DATED : June 23, 2009
INVENTOR(S) : John Q. Chen It is certified that error appears in the above-identified patent and that said Letters Patent is hereby corrected as shown below:

Column 14
Claim 11, Line 13: replace "SAPO-5, SAPO-8, SAPO-1" with --SAPO-5, SAPO-8, SAPO-11--.

Signed and Sealed this

Eighth Day of September, 2009

David J. Kappos
*Director of the United States Patent and Trademark Office*